United States Patent [19]
Olinger et al.

[11] Patent Number: 5,466,589
[45] Date of Patent: Nov. 14, 1995

[54] COATED SUBSTRATES EMPLOYING ORIENTED LAYERS OF MUTANT HEME PROTEINS AND METHODS OF MAKING AND USING SAME

[75] Inventors: Jill M. Olinger, Fishers, Ind.; Stephen G. Sligar, Urbana, Ill.; Mark A. McLean; Paul W. Bohn, both of Champaign, Ill.; Patrick Stayton, Seattle, Wash.

[73] Assignee: Biotechnology Research & Development Corporation, Peoria, Ill.

[21] Appl. No.: 945,291

[22] Filed: Sep. 11, 1992

Related U.S. Application Data

[63] Continuation-in-part of Ser. No. 615,046, Nov. 19, 1990, abandoned.

[51] Int. Cl.⁶ ............................ C12N 11/02; C12M 1/14; G01N 27/327; G01N 21/41
[52] U.S. Cl. ...................... 435/174; 435/189; 435/283.1; 435/808; 435/817; 530/385; 530/401; 530/810; 422/57; 422/70; 422/76; 422/82.01; 422/82.05
[58] Field of Search ........................ 435/174, 189, 435/288, 817, 808, 969; 436/164, 518, 801, 805, 806; 422/57, 70, 76, 82.01, 82.05; 530/385, 810, 401

[56] References Cited

U.S. PATENT DOCUMENTS

| | | | |
|---|---|---|---|
| 3,215,685 | 11/1965 | Nakanishi et al. | 530/401 |
| 3,519,538 | 7/1970 | Messing et al. | 195/63 |
| 3,642,978 | 2/1972 | Ogawa | 530/401 |
| 3,652,761 | 3/1972 | Weetall | 424/12 |
| 4,071,409 | 1/1978 | Messing et al. | 195/63 |
| 4,092,116 | 5/1978 | Giaever | 435/7.21 |
| 4,103,064 | 7/1978 | McAlear et al. | 428/333 |
| 4,234,681 | 11/1980 | Deluca-McElroy | 435/8 |
| 4,237,267 | 12/1980 | Okuyama et al. | 435/188 |
| 4,238,757 | 12/1980 | Schenck | 357/25 |
| 4,332,892 | 6/1982 | Ptashne et al. | 435/68 |
| 4,506,015 | 3/1985 | Ho et al. | 435/175 |

(List continued on next page.)

OTHER PUBLICATIONS

Vilker et al "Bacterial Cytochrome P–450 . . . On Immobilized Electrodes" *Redox Chem. Interfac. Bhav. Biol. Mol.* pp. 105–112, Plenum N.Y. (1988).
Alegria et al "Construction and Characterization of Monolayer films . . . " pp. 601–608 in *Cytochrome Syst.: Mol. Biol. Bioenerg.*, edited by Paoa et al (1987).
Conrad, "Covalent Attachment of Cobalt–Modified Cytochrome c . . . " *J. Electrochem. Soc.* 136(2):50C–53C (Feb. 1989).
Bill et al "Affinity Chromatography Purification of Cytochrome c Oxidase" *FEBS Lett.* 120(2):248–250 (Nov. 1980).
Pachence et al "Orientation and lateral mobility of cytochrome c . . . " *Biophys. J.* 58:379–389 (Aug. 1990).
Pachence et al "Location of the heme–Fe atoms within the profile structure of a monolayer . . . " *Biophys. J.* 56:327–337 (Aug. 1989),
Schubert et al, "Application of Cytochrome P–450 in . . . Enzyme Eloectrodes", *Pharmazie* 40:235–239, Apr. 1985.
Zhujun et al, "Optical Sensor . . . Immobilized Hemoglobin", *Anal. Chem.* 58:220–222, 1986.

(List continued on next page.)

*Primary Examiner*—Stephen G. Walsh
*Attorney, Agent, or Firm*—Foley & Lardner

[57] ABSTRACT

The present invention is directed to coated substrates having a coating of biological macromolecules, preferably proteins, which are capable of being immobilized on a substrate surface and have a marker. These proteins usually are mutant proteins obtained by mutagenesis of the gene encoding a random positioning protein. When a mutant protein molecule is immobilized on the substrate, the marker of the mutant protein molecule is in a select spatial relationship with both the substrate and the markers of adjacent protein molecules. A substrate coated with an oriented layer of the mutant proteins exhibits improved or different properties when compared to a substrate having a randomly positioned layer of proteins thereon.

17 Claims, 4 Drawing Sheets

U.S. PATENT DOCUMENTS

| | | | |
|---|---|---|---|
| 4,562,157 | 12/1985 | Lowe et al. | 435/14 |
| 4,572,901 | 2/1986 | Ceriani et al. | 436/528 |
| 4,581,336 | 4/1986 | Malloy et al. | 435/176 |
| 4,609,625 | 9/1986 | Keyes et al. | 435/176 |
| 4,613,541 | 9/1986 | Isoda | 428/212 |
| 4,647,544 | 3/1987 | Nicoli et al. | 436/518 |
| 4,655,885 | 4/1987 | Hill et al. | 204/72 |
| 4,666,847 | 5/1987 | Alford et al. | 435/253 |
| 4,735,906 | 4/1988 | Bastiaans | 436/527 |
| 4,778,769 | 10/1988 | Forrest et al. | 436/501 |
| 4,826,765 | 5/1989 | Greene et al. | 435/68 |
| 4,857,152 | 8/1989 | Armstrong et al. | 204/403 |
| 4,881,109 | 11/1989 | Ogawa | 435/176 |
| 4,933,285 | 6/1990 | Patton | 435/181 |
| 5,115,102 | 5/1992 | Haymore et al. | 435/69.1 |
| 5,200,051 | 4/1993 | Cozzette et al. | 435/291 |
| 5,215,882 | 6/1993 | Bahl et al. | 436/518 |

OTHER PUBLICATIONS

Conrad, "Covalent attachment . . . cytochrome c to . . . electrode", *J. Electrochem. Soc.* 136(2):50C–3C, 1989, as abstracted in *Chem. Abst.* 110:553 Ref No. 143387g (1984).

Bunji Hagihara, *The Enzymes*, vol. XI, Oxidation–Reduction, Part A, Dehydrogenases (I), Electron Transfer (I), Third Edition, 1975, pp. 572–577. (Paul Boyer, Editor).

Patrick S. Stayton, et al., Determination of Cytochrome $b_5$ Association Reactions, *The Journal of Biological Chemistry*, vol. 263, No. 27, Sep. 25, 1988, pp. 13544–13548.

Susanne Beck von Bodman, et al., *Synthesis, bacterial expression, and mutagenesis of the gene coding for mammalian cytochrome $b_5$*, Proc. Natl. Acad. Sci. USA, vol. 83, Dec. 1986, pp. 9443–9447.

Patrick S. Stayton, et al., Putidaredoxin Competitively Inhibits Cytochrome $b_5$–Cytochrome $P-450_{cam}$ Association: *A Proposed Molecular Model for a Cytochrome $P-450_{cam}$ Electron–Transfer Complex, Biochemistry*, 1989, vol. 28, pp. 8201–8205.

Lucy Netzer and Jacob Sagiv, A New Approach to Construction of Artificial Monolayer Assemblies, *J. Am. Chem. Soc.*, vol. 105, No. 3, 1983, pp. 674–676.

Dennis A. Stephens and Paul W. Bohn, Absorption Spectrometry of Bound Monolayers on Integrated Optical Structures, *Anal. Chem.*, 1989, vol. 61, pp. 386–390.

Randall A. Kok and Michael B. Hall, Bridging Ligand Effects in Quandruply Bonded Dichromium (II) Compounds, *J. Am. Chem. Soc.*, 1983, vol. 105, pp. 676–677.

R. Blankenburg, et al., Interaction between Biotin Lipids and Streptavidin in Monolayers: Formation of Oriented Two–Dimensional Protein Domains Induced by Surface Recognition, *Biochemistry*, 1989, vol. 28, pp. 8214–8221.

D. J. Walls and P. W. Bohn, Enhanced Raman Scattering at Dielectric Surfaces. 2. Molecular Orientations from Polarized Surface Raman Scattering, *The Journal of Physical Chemistry*, 1990, vol. 94, pp. 2039–2042.

Helmut Ringsdorf, et al., Molecular Architecture and Function of Polymeric Oriented Systems: Models for the Study of Organization, Surface Recognition, and Dynamics of Biomembranes, *Agnew. Chem. Int. Ed. Engl.*, vol. 27, No. 1, Jan. 1988, pp. 113–158.

James M. Pachence, et al. *The Orientation and Lateral Mobility of Cytochrome c on the Surface of Ultrathin Lipid Multilayer Films*, pp. 1–18. (Apr. 1990).

S. M. Amador, et al., *X–Ray Diffraction Studies of Protein Monolayers Bound to Self–Assembled Monolayers* (6 pages). (Feb. 1990).

James A. Wells, et al., Casseette mutagenesis: an efficient method for generation of multiple mutations at defined sites, *Gene*, vol. 34, (1985), pp. 315–323.

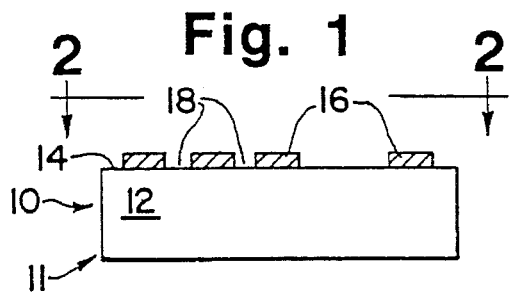
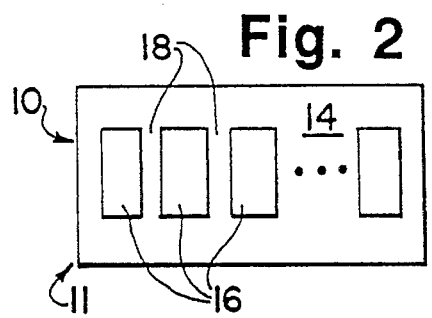
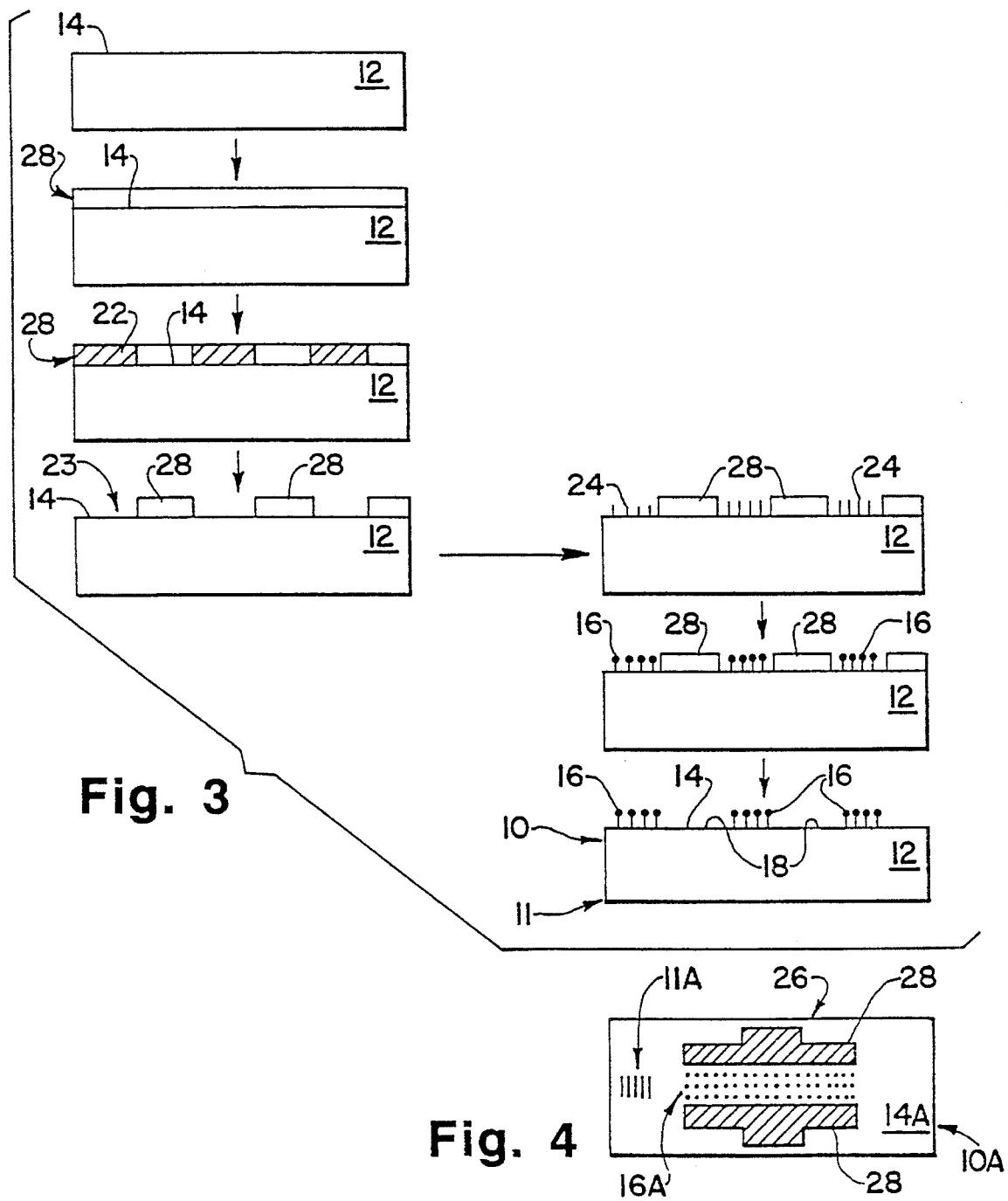

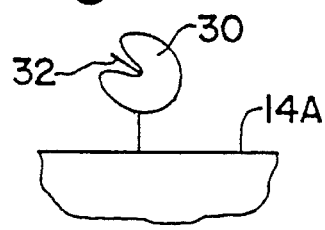
Fig. 5A
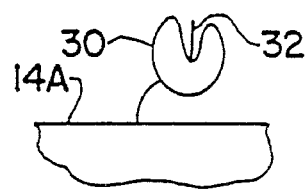
Fig. 5B
Fig. 6
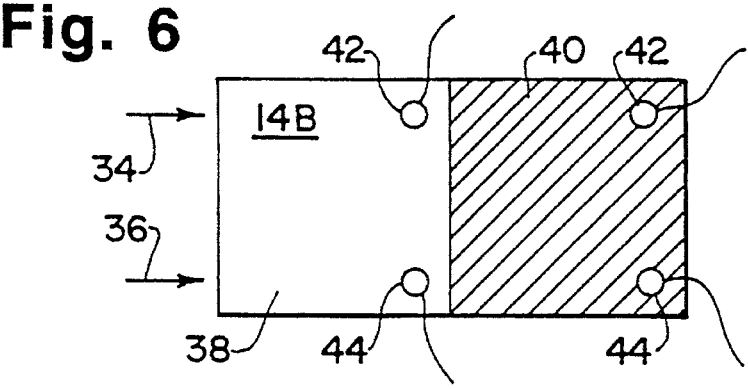
Fig. 7
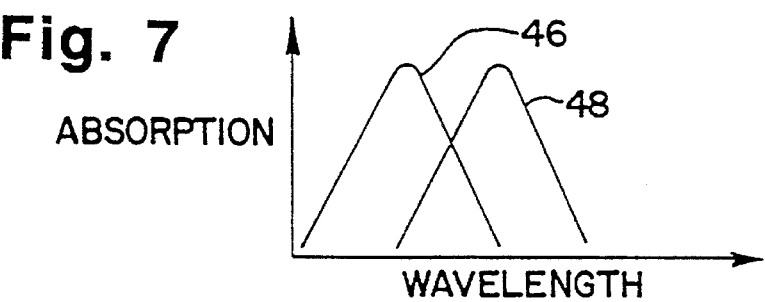
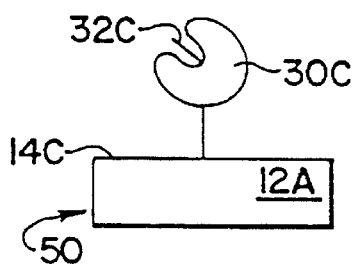
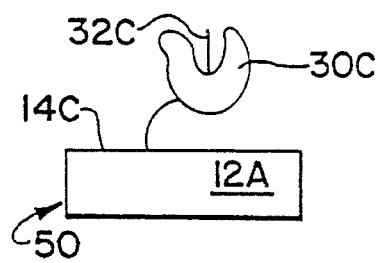
Fig. 8A               Fig. 8B

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i v ) ANTI-SENSE: YES ( x i ) SEQUENCE DESCRIPTION: SEQ ID NO:1:

GATGATGTAA CATTTCGACA GTTC        24

( 2 ) INFORMATION FOR SEQ ID NO:2:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

TTCCTCGAAT GCCACCCC        18

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i v ) ANTI-SENSE: YES ( x i ) SEQUENCE DESCRIPTION: SEQ ID NO:3:

GTTCTCGAGC GCAGGTACTA 20

COATED SUBSTRATES EMPLOYING ORIENTED LAYERS OF MUTANT HEME PROTEINS AND METHODS OF MAKING AND USING SAME

The invention described in this application was made in the course of work partially funded by the United States Department of Agriculture, Agriculture Research Service, under Grant No. 59 32U4-7-119. The United States Government may have certain rights in this invention. This application is a continuation-in-part application of U.S. Pat. application Ser. No. 07/615/046, filed Nov. 19, 1990, now abandoned.

BACKGROUND OF THE INVENTION

This invention relates to coated substrates employing oriented layers of biological macromolecules (e.g., proteins) which have a preferential binding site that is capable of coupling with functional groups on the surface of a substrate. In particular, the present invention relates to substrates coated with mutant protein molecules having, at a select position in the amino acid sequencer either an amino acid or the side chain of the amino acid replaced to create the preferential binding site, which is in a select spatial relationship to a marker on the mutant protein. The mutant protein molecules are immobilized on a substrate in a desired pattern, which includes uniform immobilization over the entire surface of the substrate. Due to the spatial relationship between the marker and preferential binding site, the markers of the mutant protein molecules of the layers are in a select spatial relationship with both the substrate and the markers of the adjacent mutant protein molecules.

Surface-immobilized proteins have had a great impact in many fields of basic research, including many industrial and medical technologies. Most of the research in this area has been directed towards controlling the overall activity of hybrid biomaterials, for example, through reversibly affecting the surrounding matrix materials or by immobilizing related proteins in close proximity to provide multi-step enzyme processing.

Systems which utilize a layer of proteins coupled to inorganic carriers are well known for many purposes, including antigen or antibody purification, assaying and detecting biological reactions and sensor operations.

In such systems, the surface of the carrier is often treated to provide an intermediate coupling agent. For example, U.S. Pat. No. 3,652,761 to Weetall teaches utilizing silane coupling agents. U.S. Pat. No. 4,071,409 to Messing et al. teaches using polymeric isocyanates and discloses other coupling agents.

Such previous systems possessed limited usefulness. It was determined that a significant advance would be realized if the immobilization process itself specified assembly and regulated function, which allows selective control of molecular recognition events or molecular activity. Because many molecular recognition processes, such as protein-protein interactions, are controlled through specificity in complementary reactive surfaces, controlling the orientation of immobilized proteins can be a straightforward means of manipulating assembly and function. Similarly, molecular activity can also affected by orientation of the molecule on the substrate.

Proteins for use with this invention can have a marker such as a heme prosthetic group, an enzyme active site, a ligand or epitope binding site, a particular amino acid sequence or the like. The efficacy and usefulness of systems employing such proteins is greatly improved where the marker of the protein molecule is positioned in a particular, select relationship to the substrate surface and the markers of adjacent protein molecules.

Heretofore, random protein and marker positioning on a substrate surface could only be obtained because the vast majority of proteins have more than one reactive residue. These proteins are random positioning proteins. In other instances, some protein molecules have only one reactive residue on its surface and therefore will naturally be oriented relative to the substrate surface and adjacent proteins. However, the position of the one reactive residue limits the protein to be oriented in only one particular manner. Such a protein is not suitable if a different orientation is desired. Proteins that do not have a residue that is reactive with the coupling agent could not be previously utilized.

Random positioning of protein molecules on a substrate surface can be deleterious in a number of applications. For instance, in systems which utilize proteins that transfer electrons or electromagnetic radiation between adjacent proteins, random positioning of these protein molecules in the layer inhibits transfer between proteins and propagation through the layer as compared to systems where proteins are mutated so that the marker of the each immobilized protein molecule is in a select spatial relationship with both the substrate surface and the markers of adjacent protein molecules. Random positioning also can reduce the absorption of light by the layer of proteins as when each protein requires the light to be incident in a direction parallel to a light absorptive marker of the protein. Additionally, random positioning can adversely influence the binding and interaction characteristics of immobilized protein.

Industry has needs which can be satisfied by coated substrates which have orientated layers of proteins. Such substrates can be produced by immobilizing mutant proteins on a substrate—these mutant proteins have a marker in a desired and select spatial relationship with a preferential binding site, which binds the protein to functional groups of a substrate.

OBJECTS OF THE INVENTION

It is therefore an object of this invention to provide coated substrates having a coating of biological macromolecules immobilized in an oriented manner thereon;

It is another object of this invention to provide a coated substrate where mutant protein molecules employed on the substrate have a marker and a preferential binding site;

It is still another object of this invention to control molecular interactions or recognition events by controlling the orientation and positioning of the protein binding or interaction structure;

It is a further object of this invention to provide a coated substrate wherein the mutant protein molecules are immobilized on the substrate via their preferential binding sites so that the markers of the mutant protein molecules are in a select spatial relationship with both the substrate and the markers of adjacent mutant protein molecules;

It is still a further object of this invention to provide a method of producing the coated substrates described above;

Other objects, features, and advantages of the present invention will be apparent from the accompanying description drawings, and sequence data.

SUMMARY OF THE INVENTION

The present invention is directed to coated substrates having a coating of biological macromolecules, preferably proteins, which are capable of being immobilized on a substrate surface. These proteins usually are mutant proteins obtained by mutagenesis of the gene encoding a random positioning protein, which often is a protein in its native state. However, a random positioning protein is not necessarily limited to native proteins; synthetic genes encoding proteins or polypeptides which closely correspond to native proteins may also be used. Mutant proteins may also be obtained by altering the side chain of a given amino acid. Mutagenesis changes the amino acid of the encoded protein at a select position. This mutation creates a preferential binding site in the resulting mutant protein; the preferential binding site has a reactive amino acid residue which is capable of coupling with functional groups on the substrate surface. The preferential binding site is in a select spatial relationship with a marker of the mutant protein. When a mutant protein molecule is immobilized on the substrate, the marker of the mutant protein molecule is in a select spatial relationship with both the substrate and the markers of adjacent protein molecules.

When the preferential binding site has an amino acid residue capable of forming a covalent bond, the functional group on the substrate surface is a nucleophilic or electrophilic functional group and coupling is by a covalent bond that is formed therebetween. Alternatively, when the preferential binding site has a charged amino acid residue, the functional group is charged functional group having the opposite charge and coupling is by electrostatic forces that are formed therebetween. Alternatively, the preferential binding site can have a specific ligand, e.g. biotin; thus, functional group would be a specific, noncovalent binding partner, e.g., avidin or streptavidin.

As stated above, the mutant proteins each have a marker. Such markers include: heme prosthetic groups, enzyme active sites, ligand or epitope binding sites, particular amino acid sequences and the like. The entire substrate surface can include a plurality of immobilized mutant proteins wherein each marker of each mutant protein molecule has the same spatial relationships in regard to the substrate surface and the markers of adjacent mutant protein molecules. This would be a coating with a uniform protein pattern. Alternatively, different portions on the substrate surface can have groups of mutant protein molecules immobilized in different select spatial relationships. In this alternative arrangement, the markers of some adjacent protein molecules will not be in the same spatial relationship with each other. Moreover, all of the immobilized protein molecules will not have their markers in the same select spatial relationship with the substrate. This type of coated substrate can be obtained by immobilizing different mutant proteins on the substrate. This would be a coating with a varied protein pattern. A varied protein pattern can also be obtained where only portions of the substrate have protein immobilized thereon.

The select position for mutation can be on or beneath the protein surface provided mutation at the select position affects the protein surface to create the preferential binding site. The select position and the position of the preferential binding site can therefore be different or the same.

Mutation, also referred to as mutagenesis, creates a preferential binding site that preferably is unique to the protein surface by replacing the amino acid at the select position with another amino acid or by replacing the side chain of the amino acid at the select position. The removed side chain preferably is replaced with a different side chain that produces a different amino acid or different binding capabilities. In addition, certain mutations can result in changes in the marker properties even if the protein is not mutated at the positions of the marker. Moreover, mutation can be undertaken in the marker of the random positioning protein to change the properties of the marker in the resulting mutant protein. Furthermore, mutation of the random positioning protein can be used create or introduce a marker in the resulting mutant protein.

The random positioning protein can have more than one site capable of coupling with a functional group. In this situation, the protein is mutated so that an amino acid at the coupling site that is not preferred is replaced with an amino acid that is not capable of coupling, or the side chain thereof is replaced, to leave only the residue at the preferential binding site available to couple. Alternatively, the protein can be mutated at an amino acid near enough to the coupling site to prohibit the amino acid residue at the nonpreferred coupling site from coupling. Therefore, the select position and the position of the preferential binding site can be different.

The random positioning protein can have an amino acid residue at the position where the preferential binding site is located that is not capable of coupling with the functional group. In this situation, the protein can be mutated at an amino acid near the position of the preferential binding site to affect the amino acid at the position of the preferential binding site and thereby create the preferential binding site. Here again, the select position and the preferential binding site are different. Alternatively, an amino acid, or the side chain thereof, at the position of the preferential binding site is replaced to create the preferential binding site. Here, the select position and the position of the preferential binding site are the same.

The mutant protein can have more than one preferential binding site as when the protein surface is symmetrical with respect to the spatial relationship between the marker and the preferential binding sites. Therefore, use of any of the preferential binding sites of such a protein having symmetry results in desired orientation of the markers in relation to the substrate surface and the markers of adjacent protein molecules.

The gene can be mutated a second time to obtain a double mutant protein having two binding sites. The additional or second binding site can be present when one binding site is preferred because it has a greater affinity for the functional group of the substrate or when one of the binding sites is blocked until after the residue of the preferential binding site couples with the functional group. Having two binding sites is useful to provide a second monomolecular layer of mutant protein molecules on the first monomolecular layer of mutant protein molecules. The mutant protein of the second monomolecular layer can also have two binding sites so that one binding site is available to bind with mutant protein molecules to form a third monomolecular layer. By using mutant proteins having two binding sites, a plurality of oriented, monomolecular layers can be sequentially built upon the substrate surface.

Furthermore, having more than one binding site can be useful when it is desired to bind a ligand or reporter group to the proteins in the layer. The ligand can affect the transfer of electrons in the layer and this change can be noted to determine the concentration of ligand present as analyate in a medium.

Representative protein types include metallo-proteins (such as heme proteins), enzymes, antibodies, antigens, and the like. In theory, any protein could be employed with this invention; however, in practice some proteins may prove difficult to immobilize or be of a nature where maintenance of an orientation is unlikely (e.g., where a protein can assume random conformations spontaneously). Furthermore, some proteins may denature or otherwise assume inactive conformations when immobilized. Thus, it must be recognized that although every type of protein should be amenable to this invention, every protein member of a given protein type might not function with this invention.

Preferred proteins include heme proteins. Preferred mutant heme proteins include mutants of cytochrome $b_5$ that have the amino acid threonine, e.g., at position 73, 65 or 8, replaced with cysteine to produce, e.g., a T73C mutant, a T65C mutant or a T8C mutant, respectively. These mutations place a unique thiol group at the designated position (73, 65 or 8 respectively). When the T65C and T8C mutant heme proteins are coupled to a substrate, the heme prosthetic group of each protein is aligned about 40° to about 60° from the normal to the substrate surface. Other preferred mutant heme proteins have their preferential binding site at position 85, 75 or 33. Alternatively, the heme protein can be mutated so that the spatial relationship between a plane dissecting the prosthetic heme group (the "heme plane") is at any predefined angle from the preferential binding site.

The heme proteins can be mutated so that the spatial relationship between the heme plane and the preferential binding site is such that when the protein is immobilized on a substrate, the plane is oriented at an angle in the range of about 40° to about 60° from the normal to the surface of the substrate. Alternatively, the spatial relationship can be selected so that the angle is chosen from the group consisting of about 0° about 90° and about 180° or at a variety of angles therebetween.

The mutagenesis of the protein to replace an amino acid or a side chain can be accomplished by conventional mutagenesis techniques that can result in complete synthesis of both DNA strands. Preferred mutagenesis techniques include cassette-style site-directed mutagenesis, polymerase chain reaction (PCR) mutagenesis and the like. To replace side chains, known methods of mutation can be employed. However, other mutagenesis techniques may be employed with departing from the scope and spirit of this invention.

The resultant mutated gene codes for the mutant protein. The mutated gene is conventionally isolated, inserted into a high copy number plasmid that directs high level heterologous protein production in the host cell and, after the desired density is achieved, a conventional purification technique is utilized to obtain the mutant proteins.

Suitable substrates are those conventionally utilized in industry for incorporation into electronic, optical and like devices. The substrates are composed of conductive metals, or, preferably, inorganic materials such as siliceous materials and metal oxides. If the mutant protein is to be immobilized for use in chromatography columns and the like, substrates such as sepharose or other synthetic or natural polymeric materials may be used.

The substrate surface can have functional groups that couple with the reactive amino acid residue at the preferential binding site of the mutant protein. Alternatively, substrates which do not possess appropriate functional groups can be provided with such functional groups. A derivatization reagent can be employed to provide functional groups as long as the substrate surface has surface groups that are reactive with the derivatization reagent. As previously discussed, the functional group can be a nucleophilic or electrophilic functional group, a charged functional group, or a specific binding functional group.

The derivatization reagents have two different kinds of reactivity, i.e., they have a group that is reactive with a surface group of the substrate and a functional group that couples with the reactive amino acid residue of the mutant protein.

The choice of the derivatization reagent can control the hydrophobicity of the surface which affects the orientation of the protein and thereby the spatial relationship of the marker to the substrate and the markers of adjacent mutant proteins. The chain length of the derivatization reagent can provide flexibility to obtain various orientations of the mutant protein.

The mutant protein can be applied to the substrate as a solution by immersion, by spin coating, by application with a doctor blade and by similar techniques. Once applied, the mutant protein is then incubated on the substrate surface for a time period effective to form the monomolecular layer. When the mutant protein of the first monolayer is a double mutant protein, a second oriented monolayer can be formed thereon by the above-described method of applying and incubating. Additional monomolecular layers can be formed by using a double mutant protein in the previous layer.

The coated substrate can be utilized in biochemical, electronic, optical and similar devices. Representative applications of the coated substrate include use as a chromatography system, potentiometric sensor, amperometric sensor, phase grating, spatial light modulator, variable integrated optical waveplate, integrated optical sensor, directional electron transfer device, a ligand concentration measuring device, and the like.

BRIEF DESCRIPTION OF THE DRAWINGS

FIGS. 1 and 2 illustrate a substrate coated with oriented, monomolecular mutant protein layers thereon;

FIG. 3 is a schematic representation of a typical lithographic sequence to produce the coated substrate of FIGS. 1 and 2;

FIG. 4 illustrates a spatial light monitor;

FIGS. 5A and 5B illustrate the effect of the electric field on the orientation of a mutant protein in the spatial light monitor of FIG. 4;

FIG. 6 illustrates an integrated optical sensor;

FIG. 7 is a graphical representation of the absorption versus wavelength curves for the integrated optical sensor of FIG. 6;

FIGS. 8A and 8B illustrate the manipulation of the mutant protein in a protein diode;

DETAILED DESCRIPTION OF THE PREFERRED EMBODIMENTS

Figure 9:
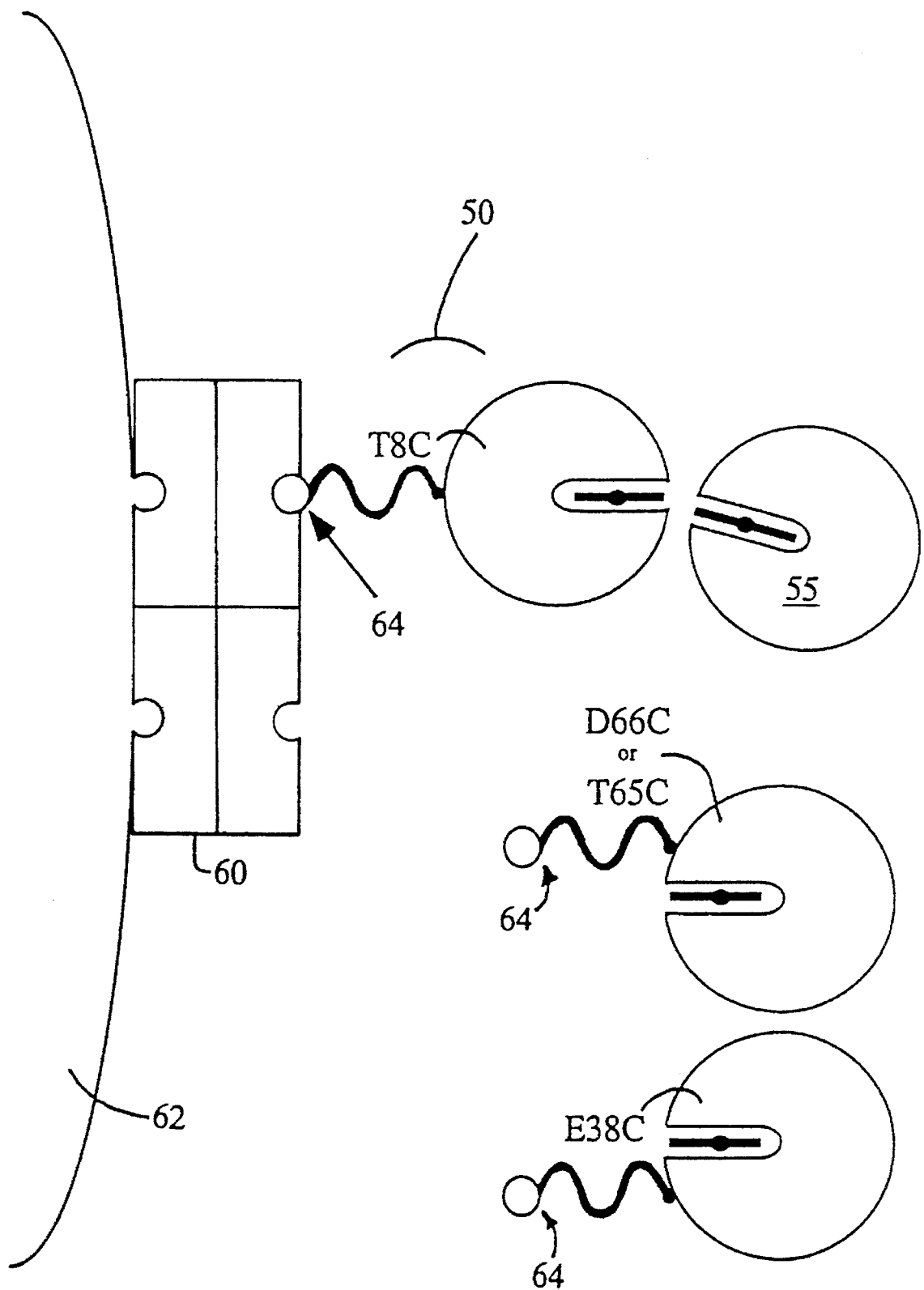
FIG. 9 is a schematic illustration of a cytochrome $b_5$ chromatography system employing T8C, T65C and D66C/E38C mutants.

Although this invention can be practiced in many different forms, there are shown in the Figures and will be described in detail presently preferred embodiments of the invention. It should be understood, however, that the present description is to be considered as an exemplification of the principles of this invention and is not intended to limit the invention to the embodiments illustrated.

The mutant protein preferably used in the present invention has an amino acid residue at a preferential binding site provided by replacing an amino acid, or the side chain of the amino acid, at a select position along the amino acid sequence of a random positioning protein. The mutant protein also has a marker at or beneath the protein surface that is in a select spatial relationship with the preferential binding site.

The term "biological macromolecule" refers to molecules of biological origin. Included are proteins, nucleic acids, lipids, polysaccharides, hormones, transmitters, factors and the like and any combination of the above.

The term "marker" refers to structures on the biological macromolecules. Where the biological macromolecule is a protein, the marker can be a heme prosthetic group, enzyme active site, ligand or epitope binding site, particular amino acid sequence, or the like. This marker can be naturally occurring on the or can be provided by mutation of the protein. Furthermore, mutation may be undertaken to alter the properties of the marker or provide a marker altogether.

The term "oriented" as used in its various grammatical forms, indicates that the spatial relationship between the marker of each biological macromolecule (e.g., mutant protein molecules) in the same layer is substantially the same, and that the spatial relationship between the markers and the substrate surface in the same layer is substantially the same.

The term "random positioning protein" as used in its various grammatical forms, refers to a protein that either does not have a binding site in a select spatial relationship with marker or has a binding site in an undesired spatial relationship with the marker, i.e., the binding site is at a nonpreferential position. A random positioning protein is often a protein in its native state; however, random positioning proteins are not necessarily so limited.

The term "select position" in regard to proteins, refers to the position along the amino acid sequence where mutation is to be undertaken. The select position can be on the surface of the protein or in the interior of the protein, i.e., beneath the protein surface. In either case, mutation at the select position affects the protein surface by creating a preferential binding site or making a binding site at a nonpreferential position nonbinding in the resulting mutant protein.

The term "select spatial relationship" concerns the spatial relationships between the immobilized biological macromolecules (e.g., heme proteins), the markers on such macromolecules (e.g., the heme prosthetic group), and the substrate. A select spatial relationship is a preferred relationship which will endow the coated substrate with the desired properties. Where the structure and/or sequence of the biological macromolecule is at least largely known, the select spatial relationships can be predetermined; thereby, resulting in a wholly rational approach to coated substrate construction. Mutagenesis of the genes encoding random positioning protein provides a preferential binding site in the resulting mutant protein at the select position or at another position by replacing the amino acid at the select position. Replacement of a side chain of an amino acid at the select position may also be undertaken, usually by known translational mutation methods, to create the preferential binding site in the resulting mutant protein.

When the random positioning protein does not have a preferential binding site, one can be introduced at the select position by replacing the amino acid, or the side chain thereof, at the preferential binding site. In this situation, the select position and the preferential binding site are at the same position along the amino acid sequence. Alternatively, the protein can be mutated at a select position that is not at the preferential binding site provided mutation affects the protein to create the preferential binding site. In this situation, the select position and preferential binding site are at different positions. When the random positioning protein has more than one binding site, a binding site that is not preferred can be removed by replacing the amino acid, or the side chain thereof, at the select position which is not the preferential binding site. Alternatively, the mutant protein can be obtained by mutation at a select position that is not at the nonpreferred binding site nor at the preferential binding site provided that the mutation only affects the protein at the nonpreferred binding site.

Representative random positioning proteins that can be subjected to mutagenesis techniques to produce the mutant proteins of the present invention include protein types such as metallo-proteins, enzymes, antibodies, antigens, ligands, structural proteins, adhesion proteins and the like.

Presently preferred randomly positioning proteins include heme proteins, which are proteins that have iron-containing ring compounds. Representative heme proteins are cytochromes b, c, a and P-450, hemoglobin, myoglobin and the like. A preferred cytochrome is cytochrome $b_5$ which is produced from a gene that was chemically synthesized in vitro, is produced in bacteria and is identical or at least substantially similar to the 89 amino acid water soluble part of rat liver cytochrome $b_5$.

The average molecular weight of the mutant protein can vary considerably. Preferably, the molecular weight is greater than about 5,000 daltons. More preferable, the molecular weight is in the range of about 10,000 to about 10 million daltons; however, the invention can be practiced with proteins outside of these ranges.

The random positioning proteins discussed herein have a sequence and structure which is at least largely known. Knowledge of the sequence and structure permits a rational approach to selecting and obtaining the mutant proteins. When the sequence and structure of the protein are known, a mutation can be undertaken to create a preferential binding site in a known location, which will cause the marker of the immobilized mutant protein to be in a predetermined spatial relationship with both the substrate surface and the markers of adjacent immobilized mutant proteins. A predetermined spatial relationship is a type of select spatial relationship. Structure of proteins can be predicted based on sequence data and can be confirmed by well-known studies such as structural nuclear magnetic resonance and X-ray crystallography. However, it is important to note that the practice of this invention is not limited to proteins which have a sequence and structure which is at least largely known. The minimum information that is required is enough sequence data to allow one of skill in the art to introduce mutations to create a preferential binding site. A series of mutations can be undertaken in a given random positioning protein or other biological macromolecule to create a variety of mutant proteins. These mutant proteins can thereafter be immobilized on a substrate. The spatial relationships between the marker of a given protein molecule with the substrate and the markers of adjacent protein molecules can then be determined or estimated by observing the properties of the coated substrate. If the coated substrate having particular mutant proteins has the desired properties, then it is reasonable to conclude that mutant protein molecules so employed afford a spatial relationship which is appropriate and therefore select. Thus, a select spatial relationship can be obtained without knowledge of the entire sequence and structure of the random positioning protein and the mutants obtained therefrom. Although this approach may require a further degree of experimentation, it can be readily performed by one of skill in the art and is not undue.

Mutagenesis techniques for replacing the amino acid are conventional. A preferred mutagenesis technique is cassette-style site-directed mutagenesis which is disclosed in Wells, et al. "Cassette-mutagenesis: an efficient method for generation of multiple mutations at defined sites" *Gene*, 34 315–23 (1985).

Another preferred mutagenesis technique is polymerase chain reaction (PCR) mutagenesis. An illustration of this technique is provide in EXAMPLE 1, below.

A representative mutagenesis technique is the "Oligonucleotide-directed in vitro mutagenesis system, version 2, Code RPN1523," of Amersham International Plc.

Alternatively, the random positioning protein can be mutated by replacing the side chain of the amino acid at the select position by conventional in vitro translation methods as disclosed in Maniatis, T. et al., eds. "Molecular Cloning" Cold Spring Harbor Laboratory, New York (1982).

Suitable techniques for mutating, cloning and expressing the protein are disclosed in Wu, R., ed., "Recombinant DNA Parts A, B and C", *Methods in Enzymology*, Volumes 68, 100 and 101, Academic Press, New York, 1979, 1983 and 1984.

The gene produced by mutagenesis codes for the protein. The mutated gene is isolated and introduced into a host cell utilizing a suitable vector system for the particular host. Suitable vector systems include all vectors with *Escherichia coli* (*E. coli*) or broad host range origins of replication, e.g., pUC, RSF1010 and the like, and contain strong promoters, e.g., lac, tac, T7, lambda and the like.

Suitable means for expressing the mutant protein include yeast, viral, Bacillus, Pseudomonas, Xenopus, mammalian, insect, and like expression systems.

A preferred host cell is E. coli. A particularly preferred *E. coli* is *E. coli* TB-1 commercially available from BRL Laboratories, Bethesda, Md. which will be used in the following discussion of the parameters of a representative expression system for a mutant cytochrome $b_5$ protein.

A representative culture media for the *E. coli* is a conventional "Luria Broth" which contains 5 grams (g) of Yeast Extract (commercially available from Difco or Sigma Chemical Co.), 10 g of casein hydrosylate (commercially available from Difco) and 10 g of sodium chloride per liter of distilled and deionized water (water).

The *E. coli* and the media are introduced into a suitable bioreactor such as a rotating drum reactor, a bubble column reactor, or the like.

The growth temperature preferably is in the range of about 35° to 45° C. Low oxygen tension preferably is utilized with mutant heme proteins since heme biosynthesis is normally repressed under strong aeration. The cells can be grown to an optical density of about 4 to about 6 under these low aeration conditions. However, optical densities above 10 can be achieved.

The mutated gene is purified by a conventional purification technique. Representative purification techniques are disclosed in Scopes, "Protein Purification Principles and Practice", Springer-Verlag, New York (1982) and Deutscher, M. P., ed., "Guide to Protein Purification" *Methods in Enzymology* Volume 182, Academic Press, New York 1979.

The mutant protein can be immobilized upon the surface of a substrate in a monomolecular oriented layer because each mutant protein has a preferential binding site.

The substrates are made of materials that are conventionally utilized in the biotechnology, chemical, electronics, optics, and other industries. However, suitable materials that are discovered in the future can also be utilized. The substrate is typically a wafer of a siliceous material or a metal oxide. Alternatively, the substrate can be a conductive metal, a polysaccharide such as Sepharose, or a functionalized mineral-derived material like mica or graphite. The substrate materials can be provided as pure crystals or can be applied to a conventional base material by a known process such a sputter coating, chemical vapor deposition, evaporation coating and the like.

The thickness of the substrate can be varied over a wide range and is primarily dependent upon the application for the coated substrate. Preferably, the substrate has a thickness in the range of about 100 micrometers ($\mu$m) to about 1 millimeter (mm).

Representative substrate materials include titanium zinc glasses, i.e., glasses containing large concentrations of titanium and zinc, fused quartz, oxidized silicon wafers, i.e., wafers exposed to steam oxidation to produce a thin film layer of silicon oxide on the surface of the silicon, aluminum oxide, indium tin oxide, tin oxide, copper oxide, lead oxide, silver oxide, nickel oxide, silicon nitrides, silver, gold and the like.

The substrate surface has thereon functional groups that are capable of coupling with the reactive amino acid residue at the preferential binding site. The functional group either occurs naturally on the surface, i.e., the functional group is a reactive functional group that is part of the substrate material, or can be provided by a derivatization reagent.

The substrate material has on its surface an effective number of either functional groups capable of coupling with the amino acid or surface groups, e.g., hydroxyl or amine groups, to react with the derivatization reagent and thereby provide an effective number of functional groups. An effective number of functional groups is that which provides the desired density of mutant proteins in the oriented monomolecular layer.

The functional group can be a nucleophilic functional group that is capable of coupling with the amino acid residue by forming a covalent bond. Alternatively, the functional group can be a charged functional group that is capable of coupling with the amino acid residue having the opposite charge by electrostatic forces that arise therebetween, or a specific binding molecule capable of forming strong, non-covalent interactions with the amino acid residue.

The derivatization reagent can be any compound that has a reactive group capable of reacting with surface groups of the substrate surface and a functional group capable of coupling with the reactive amino acid residue at the preferential binding site. For example, when the preferential binding site has a cysteine residue the functional group of the reagent can be capable of forming a thioether, disulfide, thioester or metal-sulfur bond.

Representative derivatization reagents include organomercury compounds, e.g., p-mercuriobenzoic acid and methyl mercuric iodide; organic compounds with an activated double bond, e.g., styrene; maleimide derivatives, e.g., N-ethylmaleimide and maleic anhydride; alkyl halides, e.g., 3-bromopropyltrimethoxysilane, 3-iodopropyltrimethoxysilane, 3-acryloxypropyltrimethoxysilane and 3-mercaptopropyltrimethoxysilane; metal complexes, e.g., gold, silver, copper, iron, zinc, cobalt, molybdenum, manganese, arsenic, and cadmium ions in aqueous solution; organodisulfides, e.g., bis-dithiothreitol and dithionitrobenzoic acid; organoisothiocyanates, e.g., fluorescein isothiocyanate and phenyl isothiocyanate; nicotinamide derivatives, e.g., nicotinic acid, nicotinamide and nicotinamide adenine dinucleotide; aldehydes and ketones, e.g., benzaldehyde, glyceraldehyde and methylethlylketone; lactones and lactams, e.g., penicillin, gluconolactone, glucuronolactone and uracil lactam; quinones, e.g., benzoquinone, naphthoquinone and anthraquinone; any compound with a double bond, whether or not it has beta-unsaturation, in the presence of ultraviolet (uv) or higher energy radiation, e.g., diazirenes, carbenes, and nitrenes; other organothiols, e.g., other cysteine-bearing proteins, mercaptoethanol and mercaptopyruvic acid; phosphoesters with high energy phosphate bonds, e.g., adenosine triphosphate, cyclic adenosine triphosphate, guanosine triphosphate, and cyclic guanosine triphosphate; and the like and any mixtures or combinations thereof.

Furthermore, the selection of the derivatization reagent can affect the hydrophobicity and/or ionic content of the surface which is useful in fine-tuning the orientation of the mutant protein and thereby the select spatial relationship between the marker of a given mutant protein with both the substrate and the markers of adjacent mutant protein molecules. The hydrophobicity and/or ionic content of the surface can exert a force on the mutant protein that shifts the orientation of the protein. Thus, the orientation of a mutant protein can be varied by varying the derivatization reagent. For example, the marker of a mutant protein may orient at a 60° angle with respect to the surface normal when the surface is hydrophilic. However, when the surface is highly hydrophobic, the marker may orient at a 55° angle. Thus, tailoring the surface chemistry can provide a method of fine-tuning the orientation of the protein.

The derivatization reagent can be selected to have a relatively short chain length which can provide a degree of flexibility in obtaining various orientations. Preferred chain lengths range from about 1 to 30 carbons. Flexibility can be provided by the minimization or alleviation of steric hindrances that often occur when longer chain length derivatization reagents are utilized. The steric hindrances are caused by the interaction of the longer chains and can change the orientation of the protein as compared to when the steric hindrances are not present. Although this change in orientation is desirable in some situations, it is undesirable in many situations, especially those situations wherein the orientation is expected to change in response to a stimulus.

The coated substrate can be made by the following procedure. The surface of the substrate is scrupulously cleaned prior to application of the mutant protein or the derivatization reagent. Cleaning of the surfaces of substrates of the type which are commonly used in the electronics and optical industries is preferably performed by immersing the surface, preferably the entire substrate, in three successive hot, e.g., about 160° to about 180° C., sulfuric acid baths. The immersion time in each bath is about three minutes. The surface is then rinsed with water. Optionally, the surface is then dipped in buffered hydrofluoric acid followed by a second water rinse. Next, the surface is immersed in a hot, e g , about 60° C., mixture of ammonium hydroxide: hydrogen peroxide in a volume ratio of 4:1. Subsequently, the surface is rinsed in water and blown dry with a dry, inert gas, e.g., nitrogen, that is filtered. The substrate having a clean surface can be stored in a vacuum desiccator or water until needed.

The derivatization reagent can be applied by refluxing the clean substrate in a dry chloroform solution of the derivatization reagent for a time period of about 1 to about 4 hours.

The mutant protein is preferably applied to the substrate by immersing the surface in an about 10 micromolar (μM) protein solution in an aqueous phosphate or aqueous Tris (hydroxymethyl) aminomethane buffer. The surface is then incubated in the solution for a time period effective to achieve full monomolecular layer coverage. Preferably, this time period is at least 3 hours and, more preferably, is in the range of about 6 to about 24 hours.

Alternative techniques for applying the mutant protein in solution to the substrate surface include spin coating, horizontal flow, substrate pulling and doctor blade techniques. The concentration of the protein solution varies depending upon the application technique and the specific processing conditions. Preferably, an about 10 μM to about 1 millimolar (mM) protein solution in a previously described buffer is utilized. After the protein solution is applied it is incubated on the surface for the effective time period previously disclosed.

In the spin coating technique the protein solution is applied to the surface of the substrate after which the substrate is held in a chuck, preferably by reduced pressure, and is spun at a relatively high rotational speed, e.g., about 1,000 to about 10,000 rpm, for a relatively short time period, e.g., about 5 to about 60 seconds.

In the horizontal flow technique a horizontal substrate surface first is coated with a solution of the protein, the substrate is rotated to position the surface in a vertical position and the majority of the solution is permitted to drain off of the surface.

In the substrate pulling technique the substrate is immersed in a tank containing the protein solution and is slowly removed from the tank as by a motor-driven pulley or conveyor belt system.

In the doctor blade technique the protein solution is applied to the surface of the substrate, a sharp edged blade is positioned at a desired height, e.g., about 50 to about 500 μm, above the surface, and excess solution is removed by contact with the blade as the substrate is moved under the blade or the blade is moved over the substrate.

After incubation, the surface can be rinsed to remove multiple layers of mutant protein held to the surface by weak physiosorption forces and thereby obtain the desired oriented monolayer of mutant proteins. The rinsing step can include rinsing with pure buffer for about 10 minutes followed by rinsing with water for about 10 minutes.

The thickness of a monomolecular layer is dependent upon the dimensions of the individual mutant protein molecules. For example, a monomolecular layer of the mutant heme protein cytochrome $b_5$ has a thickness of about 30 Angstroms (Å).

The coated substrate of the present invention has many applications including as sensors and conductive devices. The energies sensed or conducted include electricity and electromagnetic radiation (especially light). Representative applications include potentiometric sensors, amperometric sensors, bipolar transistors, semiconductor or other electrodes, piezoelectric crystals, thermoelectrical crystals, charge-coupled devices, opto-electronic devices such as integrated optics and waveguide sensors, nonlinear optical devices, fiber optic devices, surface plasmon resonance-based sensors, magnetic sensors and the like.

More particularly, the aforementioned mutant heme proteins can be utilized as a phase grating, spatial light modulator, variable integrated optical waveplate, integrated optical sensor, directional electron transfer device and the like. Some of these uses are discussed hereinbelow.

As illustrated in FIGS. 1 and 2, a coated substrate 10 can be used as a phase grating 11 wherein a substrate 12 has on a substrate surface 14 oriented, monomolecular mutant protein layers 16. The heme prosthetic group of the proteins is preferably oriented substantially parallel to the surface 14. Next to the layers 16 are open spaces 18.

The phase grating is generated by arranging the layers 16 in an alternating fashion on the substrate surface 14; thus, causing the imaginary portion (absorption) of the refractive index to vary in a periodic fashion. This alternating fashion produces a surface 14 that has absorbing regions adjacent to nonabsorbing regions. The absorbing regions are coated with the oriented protein layer 16 while the nonabsorbing regions are not coated (like open spaces 18) or are coated with a nonabsorbing protein or other nonabsorbing material. The size of the regions are preferable in the range of about 0.05 to about 5 μm wide, about 100 to about 1,000 um long and about 30 to about 300 Å thick. The size of adjacent regions can be alike or different and can be varied to adjust the coupling properties, e.g., to improve the coupling efficiency at a specific wavelength or in a given direction, of the phase grating.

To achieve an absorbing situation, which would be desired for the phase grating application, the light used would be polarized such that its electric vector is parallel to the surface, i.e., traverse electrical radiation would be utilized. Alternatively, if the protein is oriented such that the absorbing group is primarily oriented perpendicular to the surface, the radiation would be chosen to be transverse magnetic polarized. Phase gratings are typically utilized as analogues to mirrors in integrated optical devices and as couplers, which are components that switch light into and out of the thin film waveguide.

FIG. 3 is a schematic representation of a typical sequence utilized to produce the phase grating 11. A silicon dioxide substrate 12 has applied thereto a conventional photoresist coating 28. A desired pattern of the phase grating is conventionally exposed in the photoresist coating 28 to produce exposed areas 22. Development of the exposed areas 22 results in the substrate surface 14 being revealed in the developed areas 23. A derivatization reagent is applied to the substrate surface 14 to produce a derivatized surface 24. The functional groups of the derivatization reagent couple with the amino acid residues of the mutant proteins to produce the monomolecular oriented layers 16. The remainder of the photoresist coating 28 is conventionally removed to produce a coated substrate 10 having monomolecular layers 16 with open spaces 18 therebetween.

FIG. 4 is a schematic representation of a spatial light modulator 26 utilizing a coated substrate 10A. On a substrate surface 14A are positioned two opposed, spaced electrodes 28 having an oriented protein layer 16A therebetween. A phase grating 11A, or other coupling structure, can be present to couple light into the protein layer 16A of the spatial light modulator 26. The orientation of the immobilized proteins can be manipulated by imposing external perturbations, e.g., AC or DC electric fields, or the presence of a phase grating radiation pulse. Furthermore, manipulation can also be effected by the presence or absence of salts or chaotropic agents in a solvent on the spatial light modulator or the presence of small molecule ligands that bind to the heme groups.

An individual protein 30 in the protein layer 16A of the spatial light modulator 26 is illustrated in FIGS. 5A and 5B. As shown in FIG. 5A, when the electrical field is off, the protein 30 is in a position in which the interaction with the propagating light radiation field is strong because a schematically represented plane 32 dissecting the heme prosthetic group ("the heme plane") is substantially parallel to the surface 14A. In contrast, as shown in FIG. 5B, when the electric field is on, the interaction with the propagating light radiation field is weak because the heme plane 32 is substantially perpendicular to the surface 14A. That is, when the electric field is off, the proteins are in an absorbing configuration (FIG. 5A), and when the electric field is on the proteins are in a nonabsorbing configuration (FIG. 5B). Alternatively, the mutant proteins can be tailored so that when the electric field is off, the proteins are in a nonabsorbing configuration and when the electric field is on the proteins are in an absorbing configuration. Thus, the spatial light monitor can be utilized in signal generation/processing since the presence or absence of light can stand for a 0 or a 1, which is a basis for digital logic.

When the coated substrate is utilized as a variable integrated optical waveplate it has a physical structure similar to that shown in FIG. 4. An important function in integrated optics for which waveplates are used is the incorporation of mechanisms for manipulating the polarization state of the light in the device. The mutant heme protein can act both as an absorber and as a birefringent material, i.e., the refractive index of the protein is different in all three spatial directions. Thus, if the mutant heme protein is coated onto the substrate and the radiation is propagated at a wavelength at which the heme is not strongly absorbing, then changing the orientation of the protein changes the refractive index affecting by the light propagating in the protein layer. The change in refractive index consequently changes the phase delay of the light for each of the orthogonal polarization components. This would require that the propagating radiation (light) have its electric vector not oriented along the optic axis of the oriented protein monolayer. A difference between the spatial light monitor and the variable integrated optical waveplate is that for the waveplate careful attention would be paid to the polarization state of the light and radiation would be propagated at a nonabsorbing wavelength. The relative retardation of the two components desired can be varied by simply changing the length over which the radiation sees a specific protein orientation.

When the coated substrate is utilized as an integrated optical sensor, the specific ligand-binding properties of the proteins are taken advantage of. For example, a synthesized myoglobin (hereinafter "wild-type") closely corresponding to sperm whale myoglobin, the only difference being that the product of the synthetic gene retains the N-terminal initiating methionine, is mutated twice to produce a H64L/A125C double mutant. The H64L/A125C designation means that the mutant was obtained by mutations which resulted in a leucine at position 64 rather than a histidine and a cysteine at position 125 rather than an alanine. This double mutant is thereafter immobilized on the substrate surface to produce an oriented layer. The mutant myoglobin protein binds carbon monoxide preferentially to oxygen whereas the "wild-type" myoglobin binds both carbon monoxide and oxygen with near equal affinity. When the ligand is bound, the wavelength of strongest absorption shifts dramatically. The shift is up to a 40 nanometer (nm) in favorable cases. The transmission of a laser light of the appropriate wavelength is monitored through the sensor. When some of the myoglobin proteins bind carbon monoxide, their wavelength of maximum absorption will shift and the transmitted light intensity will change.

As illustrated in FIG. 6, the integrated optical sensor can be implemented in a double-beam configuration in which two lasers (not shown) are used. One laser beam 34 has the wavelength that is transmitted by the heme protein with no bound ligand, and the other laser beam 36 has the wavelength that is transmitted by the heme protein with the bound ligand. The substrate surface 14B has an uncoated area 38 and a region 40 having an oriented, monomolecular double mutant heme protein layer. Two pairs of fiber optic probes 42 and 44 are mounted close to the substrate surface 14B. Fiber optic probes 42 measure the transmission of light having the wavelength transmitted by the unbound protein and fiber optic probes 44 measure the transmission of light having the wavelength transmitted by the bound protein. The ratio of transmission of the light from the two lasers is used as a signal as illustrated in FIG. 7. Curve 46 is for the absorption versus wavelength for the transmission of light through the unbound protein. Curve 48 is for the absorption verses wavelength for the transmission of light through the bound protein.

Alternatively, the integrated optical sensor can be implemented in a single beam configuration (not shown) in which the light initially is completely transmitted by the layer. Binding of carbon monoxide then shifts the absorption away from the wavelength of the propagating radiation and this shift is measured.

The rate of transfer of an electron through a heme protein is dependent upon the path the electron is traveling. Furthermore, the rate of electron transfer also is dependent upon the orientation of the protein to which the electron is being transferred. Thus, by adjusting the orientation of the protein through which the electron is to be transferred and of the protein to which the electron is to be transferred the rate of electron transfer can be adjusted.

For example, the fastest direction of electron transfer of a heme protein is parallel to the heme plane. Thus, as illustrated in FIG. 8A, a protein diode 50 can be produced when a substrate 12A preferably is an electrically conductive material. A heme protein 30C having a heme plane 32C is immobilized on the surface 14C oriented so that the heme plane 32C is not perpendicular to the surface 14C when the diode 50 is turned off. Thus, electron transfer is slow in the direction perpendicular to the substrate surface 14C. However, as illustrated in FIG. 8B, when the diode 50 is turned on the protein 30C is displaced so that the heme plane 32C is perpendicular to the substrate surface 14C. Thus, electron transfer is relatively fast in a direction perpendicular to the substrate surface 14C.

The following Examples are given by way of illustration, and not limitation, of the present invention.

Although the EXAMPLE 1 utilizes primers, reagents, conditions and the like to generate the T73C mutant protein of cytochrome $b_5$, other mutant proteins can be produced using this technique to mutate other proteins using different primers, reagents, conditions and the like. Production of the aforementioned T8C and T65C mutant cytochrome $b_5$ is discussed in Stayton et al. *Biochemistry* 28:8201–8205 (1989); Stayton et al. *J. Biological Chemistry* 263:13544–13548 (1988); Beck von Bodman et al. *Proc. Natl. Acad. Sci. USA* 83:9443–9447 (1986).

EXAMPLE 1: GENERATION OF T73C CYTOCHROME $b_5$ MUTANT BY A PCR MUTAGENESIS TECHNIQUE

A site-directed mutation was engineered into a gene that codes for the desired protein by using three primers in two consecutive rounds of PCR amplification. The substrate DNA was the synthetic cytochrome $b_5$ gene cloned into a pUC 19 plasmid. Of the three primers necessary for this, one primer was specific for the desired mutation, i.e., the mutagenic primer, whereas the other two primers flanked the gene by annealing to the plasmid and therefore needed only to be specific for sequences of the vector, i.e., the pUC plasmids. Therefore the choice for the latter two primers was the sense and antisense sequencing primers, i.e., universal and reverse, both of which are commercially available from sources such as New England Biolabs. Alternative vectors may also be used and the flanking primers would then have to correspond to sequences of the selected alternative vector. The mutagenic primer is preferably about 18 to 24 nucleotides long and code for the desired amino acid substitution(s) plus any other base alterations necessary for screening, e.g., colony hybridization or restriction site gain or loss. In the first PCR round, using the mutagenic primer and one of the flanking primers (the 3' ends of the primers need to face one another), a portion of the gene which now contains the desired mutation was amplified. This mutated gene fragment then served as one primer, along with the other flanking primer, in the second PCR round which amplified the entire mutated gene. Subsequent digestion with the appropriate restriction enzymes facilitated ligation of the mutated gene into the vector of choice for direct screening, sequencing and expression.

The mutagenic primer had the nucleic acid sequence 5' GATGATGTAACATTTCGACAGTTC 3' (SEQ ID NO:1). This primer was an anti-sense primer; however, mutations can be accomplished using mutagenic sense primers. The mutagenic primer was stored in ammonium hydroxide which was removed and the DNA resuspended in water, ethanol precipitated, washed, dried, and brought up in water.

A. PRIMARY PCR

To a 500 microliter (µl) eppendorf tube was added the following reagents in this order: 83 µl water (to make 100 µl total); 10 µl 10x Polymerase Buffer (supplied by the Vent polymerase manufacturer); 2 µl dNTP's (10 mM in each dNTP); 1 µl mutagenic primer, described above; 1 µl of commercially available universal primer (10 µM stock); 1 µl template, i.e., cytochrome $b_5$, 30 ng total; and 2 µl Vent polymerase (2 units) commercially available from New England Biolabs. The reagents were mixed thoroughly by finger flicking the tube, spun down and placed in a PCR machine, i.e., a commercially available DNA Thermal Cycler from Perkin-Elmer, Cetus. The reagents in the tube were subjected to 15 heating cycles in the PCR machine. One heating cycle consisted of 2 minutes at 94° C., 2 minutes at 50° C. and 2 minutes at 72° C.

A 20 µl aliquot was removed for observation and isolation by conventional electrophoresis on a 1.2% TAE agarose gel. Geneclean (Geneclean II kit, commercially available from Bio 101, LaJolla, Calif.) was used to isolate the primary PCR band, and hence the primary PCR product, from the gel.

B. SECONDARY PCR

To a 500 µl eppendorf tube was added the following reagents in this order: 62 µl water; 10 µl 10X Polymerase Buffer (supplied by the Vent polymerase manufacturer), 2 µl dNTP's, 10 mM in each dNTP 20 µl of the above Genecleaned primary PCR product; 1 µl reverse sequencing primer (10 µM stock); 3 µl template plasmid, i.e., cytochrome $b_5$, 90 ng total: and 2 µl Vent polymerase.

The reagents were mixed thoroughly by finger flicking the tube, spun down and subjected to the 15 heating cycles in the PCR machine as described in conjunction with the primary PCR.

C. LIGATION AND TRANSFORMATION

The secondary PCR reaction was ethanol precipitated by adding 10 µl of 3M sodium acetate and 200 µl ethanol at 70° C. for 15 minutes. The pellet was washed with 70% ethanol and dried. After reconstitution the DNA was digested with Pst I and Eco RI restriction enzymes in a solution of 86 µl water, 10 µl 10X restriction buffer, 2 µl Pst I, and 2 µl Eco RI at a temperature of 37° C. for a time period of 1 hour.

Similarly, 5 µl pUC19C (5 µg) was digested using a solution of 81 µl water, 2 µl Pst I, and 2 µl Eco RI at a temperature of 37° C. for a time period of 1 hour.

The reaction products were ethanol precipitated, washed, and dried to obtain pelleted products. The pellets were combined in 15 µl water, 4 µl 5X ligase buffer and 1 µl T4 DNA ligase and the resultant product was incubated at 16° C. overnight to produce the ligation mixture.

Competent cells were prepared by resuspending a TB-1 *E. coli* culture (0.3 OD) in 100 mM calcium chloride.

Transformation of the ligation mixture was conducted by incubating the ligation mixture with 200 µl of competent cells on ice for 20 minutes. This mix was then heat shocked at 37° C. for one minute and 1 ml of Luria Broth media added. After 40 minutes at 37° C., 100 µl was plated on X-Gal plates After overnight incubation of 37° C., colonies were visible on the plates.

D. SELECTION AND SCREENING

White colonies were picked and used to inoculate 5 ml overnight cultures for miniprep plasmid purification. Miniprep isolation of plasmid yielded templates for sequencing. Dideoxynucleotide sequencing using a commercial sequencing kit resulted in the confirmation of successful mutant generation T73C cytochrome $b_5$. The cells were red indicating that holo cytochrome $b_5$ was produced. Frozen stocks of the T73C mutant were prepared and used to ferment.

E. FERMENTATION BIOREACTION AND PURIFICATION

Fermentation (bioreaction) of the T73C mutant was conducted in a New Brunswick 12 liter fermentation vessel and in 6×3 liter shaker flasks which yielded 70 g of wet cells.

The T73C mutant protein was purified utilizing the following process. The plate colonies were cultured and introduced into two 5 ml cultures at a temperature of 37° C. for a time period of 16 hours. The 5 ml cultures were then introduced into 250 ml cultures with 50 mg Ampicillin and grown at 37° C. for 16 hours. The 250 ml cultures were introduced into a 25 liter fermentor and maintained therein under growth conditions for a time period of 16 to 24 hours. Cells were then harvested and subsequently frozen at a temperature of −70° C. Next, the cells were thawed at room temperature in lysis buffer and stirred in the lysis buffer at a temperature of 5° C. for a time period of 16 hours. The lysate was then centrifuged at a temperature of 5° C. at 10,000 ×G for a time period of 20 minutes. The pellet and supernatant were separated and the supernatant was saved. The pellet was resuspended in lysis buffer at a temperature of 5° C. and stirred for a time period for 2 hours. This lysate was centrifuged at a temperature of 5° C. at 10,000 ×G for a time period of 20 minutes. The resultant pellet was discarded and the supernatant saved. The supernatants were pooled and then passed through an ascending DEAE cellulose column (0–0.25M salt gradient). A concentrate first column pool was obtained by ultra filtration and subjected to gel filtration on a Bio gel p-60 resin followed by passing through an ascending DEAE cellulose column (0–0.25M salt gradient). The resulting product, purified T73C cytochrome $b_5$ mutant protein, was then evaluated for purification using SDS-page gel electrophoresis.

EXAMPLE 2: PREPARATION OF A COATED SUBSTRATE WITH AN ORIENTED LAYER OF PROTEINS

A substrate was treated with the derivatization reagent bromopropyltrimethoxysilane (hereinafter "silane") and then coated with T8C mutant heme protein.

The substrate utilized was lab craft microscope cover glass, commercially available from Curtis Matheson Scientific, Inc., catalog No. 266-809, 1 oz that were 24×60 mm in dimension and had a #1 thickness. To clean the substrate, three baths of sulfuric acid which had been heated to a temperature of about 180° C. for about one hour were prepared. The substrate was immersed in each bath for a time period of about 3 minutes before being moved to the next bath. After the third bath, the substrate was rinsed with water for a time period of 1 minute. Then, the substrate was immersed in a hydrogen peroxide/ammonium hydroxide mixture that had a volume ratio of about 1:4, respectively. The mixture had been heated to about 50° C. for a time period of about 20 minutes prior to immersion of the substrate. The substrate was immersed in the mixture for a time period of 3 minutes, removed therefrom, rinsed with running water for a time period for 1 minute and then dried with dry nitrogen.

The cleaned substrate was then annealed in preparation for the linear dichroism experiment by placing the substrate in a conventional tube furnace in a flowing high purity argon stream, turning the heat control of the furnace to high and switching the furnace off when it had reached a temperature of about 500° C. The furnace with the substrate therein was permitted to cool about 3 hours before the substrate was removed and stored in a moisture-free environment.

Next, the substrate was treated with silane and dry, distilled chloroform. The substrate, 300 ml of chloroform and 3 ml of the silane were introduced into a conventional reflux vessel. The contents of the vessel were heated to a temperature in the range of about 55° C. to about 60° C. for a time period of about 2.5 hours. Additional chloroform was introduced into the vessel to maintain coverage of the substrate. At the end of this time period, the contents of the vessel were permitted to cool for a time period of about one-half hour. The substrate was then rinsed in chloroform and dried with nitrogen.

An oriented layer of the T8C mutant heme protein was then formed on the substrate by the following procedure. A sample chamber was made using poly(tetrafluoroethylene) (commercially available as "Teflon"). The interior of the chamber had a depth of about 30 mm and a width of about 24 mm and was capable of holding half of the substrate and about 2.5 ml of a mutant protein-containing solution. Thus, half of the substrate was coated in the chamber.

A 300 µM stock of the T8C mutant heme protein was diluted to about 20 µM utilizing a pH 7.5, 50 mM potassium phosphate buffer to produce the mutant protein-containing solution.

The chamber was filled with the mutant protein containing solution and half of the derivatized substrate was inserted therein. A beaker was positioned over the chamber to limit evaporation. The substrate was maintained in the chamber for a time period of about 3 hours at about room temperature, i.e., about 20 to about 30° C. The substrate was removed from the chamber and placed in a small beaker of the potassium phosphate buffer for a short time period. Then, the substrate was rinsed with water and dried with nitrogen.

The heme of the protein was utilized to quantatively measure the amount of protein present. This measurement required that the heme be released into a solution and complexed with pyridine to form a complex that could be assayed after being reduced with a reducing agent, such as dithionite. A release solution was prepared by admixing in a suitable vessel 3 ml of the 50 μM potassium phosphate buffer, 0.5 ml pyridine and 0.25 ml of a 1M solution of sodium hydroxide. About 2 ml of the release solution was introduced into a clean chamber and then the coated substrate was introduced into the chamber. The release solution was pipetted onto the upper parts of substrate that were not immersed. The substrate was removed and the release solution containing complex was equally divided and placed into two 1 ml cuvettes. The cuvettes were optically balanced on a Hewlett Packard 7470 Spectrophotometer and then a grain of dithionite was added to the sample cuvette and the spectrum was taken.

The extinction coefficient ($\epsilon_{mm}$ 557–574) for the pyridine-heme complex is about 34.4 mM$^{-1}$ cm$^{-1}$. The number of moles of the pyridine-heme complex, which equals the number of moles of heme group and also the number of moles of protein, on the substrate was calculated utilizing the following equation:

$$\frac{(0.0049 \text{ Absorbance/cm} - 0)}{34.4 \text{ mM}^{-1} \text{ cm}^{-1}} = 0.14 \text{ μM}$$

The actual number of heme molecules was calculated utilizing the following equation:

(0.14 μMoles/1000 ml)×2 ml×(1 mole/10$^6$ μMoles)×6.02×10$^{23}$ molecules/1 mole)=1.7×10$^{14}$ heme molecules per monolayer.

The theoretical number of protein molecules on the substrate, assuming a close packed protein layer, was calculated as follows:

(2×30 mm×24 mm)×(10$^{14}$ Å$^2$/1 mm$^2$)× [1 cytochrome b$_5$/(30 ×2 Å$^2$)]=2×10$^{14}$ cytochrome b$_5$ protein molecules per monolayer.

The numeral 2 in the multiplier "2×30 mm×24 mm" is necessary because both the front and the back of the substrate were coated.

The percent coverage is determined by dividing the actual number of heme molecules by the theoretical number of protein molecules that should be present in a close packed monolayer. Thus, for the first substrate the actual percent coverage is: 1.7/2×100 =85% actual coverage.

A second substrate prepared utilizing the above procedure had a spectrum reading of 0.003 A and therefore the concentration of the release solution containing the complex was 0.087 μM. For the second substrate, the percent coverage was 61%.

EXAMPLE 3: A CYTOCHROME b$_5$ IMMOBILIZATION SYSTEM

The cytochrome b$_5$ immobilization system depicted in FIG. 9 is a means for examining and controlling protein-protein interactions. These interactions are of crucial importance to important biological processes such as electron transfer and vectorial proton transfer; thus, manipulating macromolecular specificity at interfaces is an important step toward controlling function and self-assembly in a wide variety of immobilized protein systems.

The system schematically depicted in FIG. 9 employs the cytochrome b$_5$/cytochrome c electron transfer pair. Immobilized T8C cytochrome b$_5$ (50) is shown interacting with cytochrome c (55). Molecules representing the E38C immobilization and the D66C or T65C immobilizations are depicted nearby for comparison purposes. The E38C and D66C immobilizations were obtained using the E38C/D66C double mutant discussed at length below.

Extensive biochemical, biophysical, theoretical and genetic investigations have provided a detailed understanding of the interaction surfaces for both cytochromes b$_5$ and c. The complementary binding interface between the two molecules places their heme edges in close proximity for fast electron transfer between the redox centers.

As shown in FIG. 9, three cytochrome b$_5$ mutants were employed, namely: the previously-discussed T8C and T65C mutants and the double mutant D66C/E38C. The D66C/E38C double mutant has aspartic acid replaced by cysteine at position 66 and glutamic acid replaced by cysteine at position 38.

The D66C/E38C double mutant was generated by a method which was somewhat different than the method used to produce the T8C and T65C mutants, described above. To generate the D66C/E38C mutant, two oligonucleotide primers encoding the position 66 mutation and position 38 mutation were used to amplify the gene segment that contains the mutations. The E38C mutagenic primer has the sequence of 5' TTCCTCGAATGCCACCCC 3' (SEQ ID NO:2); the D66C mutagenic primer has a sequence of 5' GTTCTCGAGCGCAGGTACTA 3' (SEQ ID NO:3). This PCR product was used in a second PCR reaction in conjunction with a universal sequencing primer, which is commercially available from sources such as New England Biolabs, to amplify the 3' end of the mutated gene (the C-terminal end of the protein). This PCR product was used with the reverse universal sequencing primer, which is also commercially available from sources such as New England Biolabs, to amplify the entire gene. This final PCR product was digested with the appropriate restriction enzymes and ligated back into the vector.

The T65C provides a preferential binding site that is close to the cytochrome b$_5$/cytochrome c binding interface, yet apparently remains sufficiently spatially distinct to prevent steric interference. The T8C mutant provides a preferential binding site on the surface opposite the exposed heme edge, at a site distant from the binding interface. Linear dichroism measurements of the prosthetic heme group demonstrate that the T65C and T8C mutants are differentially orientated at the substrate interface when immobilized. The D66C/E38C double mutant has two free thiol groups (from the two cysteine residues) which are free for binding; thus, the double mutant can be bound on either side of the heme edge. However, the percentage of protein bound via either site is presently not known, but such knowledge is not required for the practice of this invention. Both binding sites in this double mutant are relatively close to, yet sterically distinct from the cytochrome b$_5$/cytochrome c binding interface.

The system of FIG. 9 can be used for chromatography. Avidin (60) immobilized on sepharose 6B (62) was chosen as a support because it has a high pI (~10.2), which disfavors nonspecific electrostatic interactions between avidin and cytochrome c. The three mutant cytochrome b$_5$ proteins (T8C, T65C, and D66C/E38C) were biotinylated (64) with N-iodoacetyl-N-biotinylhexylenediamine (Pierce Pharmaceuticals). Excess biotin label was removed by passage over a Sephadex G-25 (Pharmacia) gel filtration resin. The biotinylated cytochrome b$_5$ was mixed with avidin immobilized on the Sepharose 6B and stirred extensively to obtain a homogeneous protein concentration throughout the resin. Chromatography columns employing this system were integrated with a Pharmacia FPLC pump system.

Equilibrium binding isotherms were obtained for the three mutants with linear potassium chloride elution gradients and corrected for small differences in cytochrome b$_5$ concentration. These isotherms were obtained as follows: 0.3 nmoles of each mutant cytochrome $b_5$ were loaded onto a 730 µl column (Pharmacia HR 5/5 containing the cytochrome $b_5$ resin) pre-equilibrated in 1 mM KPi pH=7.0 (3 columns each with a mutant plus 1 control column). A linear 0 to 100 mM KCl gradient over 30 ml was run at a flow rate of 0.75 ml/minute and the elution profile was calculated using the area under the elution peak (monitoring absorbance at 405 nm, with the total area reproducible to within 5%). The midpoint of the cytochrome c elution profile was reproducible to a standard deviation of +/−1 mM with all three cytochrome $b_5$ columns. To normalize the binding isotherms to cytochrome $b_5$ concentration, the heme content was determined (1:1 heme to cytochrome $b_5$) A solution of 20% pyridine/200 mM NaOH was passed through the column and the effluent collected. The heme concentration was determined with the pyridinehemochromogen assay using an extinction coefficient of 23.98 for $\epsilon$ (556–538)(Reduced-Oxidized).

Figure 10:
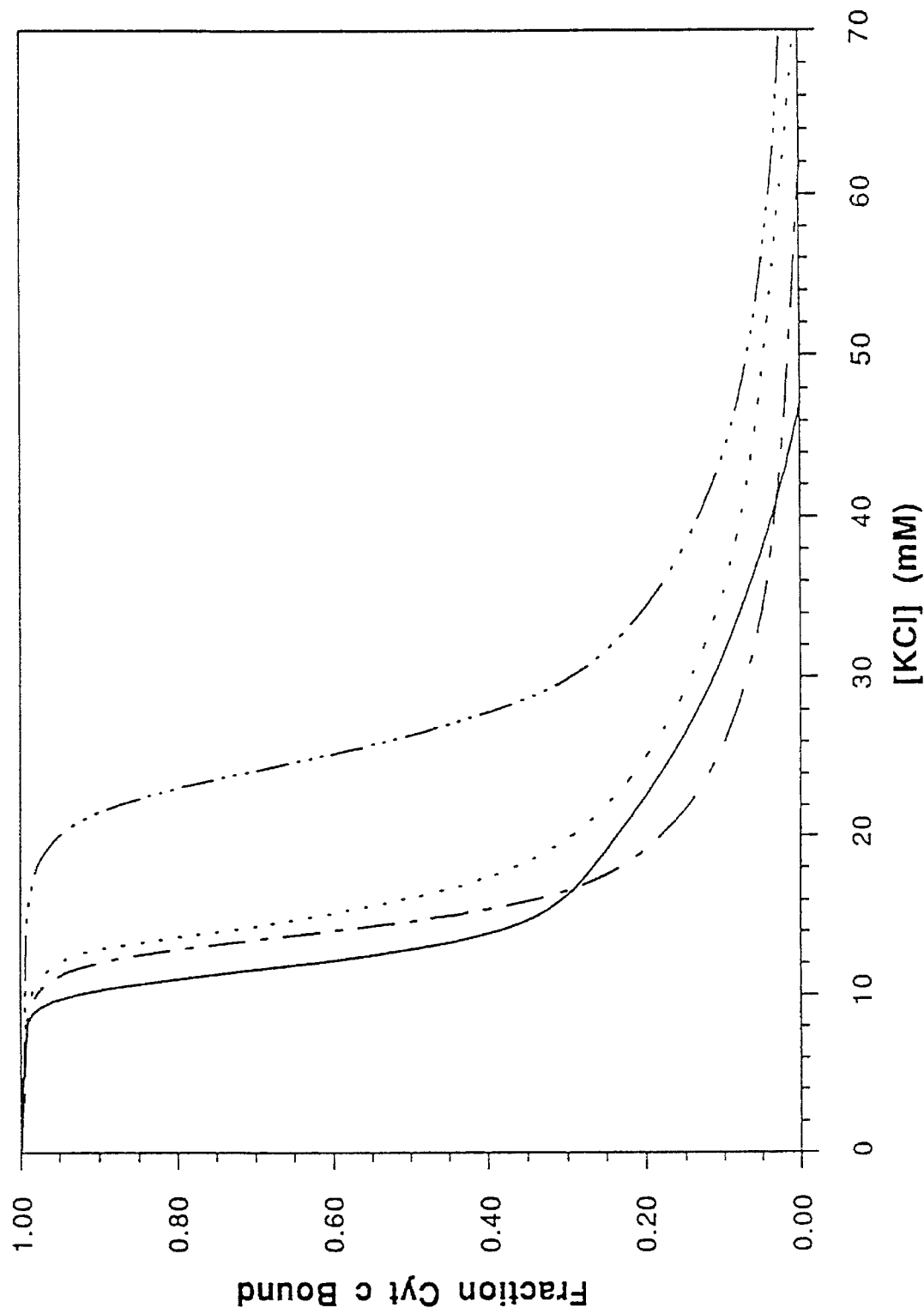
FIG. 10 depicts the orientation specific equilibrium binding isotherms of the T8C, T65C, and D66C/E38C cytochrome $b_5$ mutants.

FIG. 10 is a graphical representation of the binding isotherms for the cytochrome $b_5$ mutants. The isotherms were determined by the elution profiles generated with the linear KCl gradient. The 3 mutants and control are represented in FIG. 10 as follows: T8C (-- . . . --); T65C (-- - --); D66C/E38C ( . . . ); control, no cytochrome $b_5$ (---). The striking dependence of cytochrome c affinity on the cytochrome $b_5$ attachment site can be readily observed. Consistent with previous measurement of differential T8C and T65C orientations at surface immobilization sites, these mutants display distinct binding isotherms. Further, the reduction in cytochrome c affinity with the T65C and D66C/E38C mutants is in the direction expected for orienting the cytochrome $b_5$ binding surface toward the immobilization interface. The T8C data is consistent with an orientation which allows for substantial cytochrome c interaction. Control measurements of the binding isotherm for cytochrome c-avidin interactions (---) show that the T65C and D66C/E38C association constants are slightly higher than the non-specific background, indicating that some low affinity cytochrome $b_5$-cytochrome c interactions are retained with these mutants. These results, in combination with previous documentation indicating that cytochrome c binds close to, but sterically distinct from the T65C and D66C/E38C positions, strongly suggest that orientation dependent molecular recognition has been achieved with such a immobilized protein system.

Orientational control of protein-protein molecular recognition at interfaces will be important in two crucial interrelated aspects of device design, namely protein function and molecular assembly. Protein function is often exquisitely sensitive to the spatial relationships of subunits and protein partners. Pioneering work, disclosed herein, has demonstrated the utility of immobilization as a technique for generating spatially localized systems. Specific orientation of macromolecules, e.g., proteins, on a substrate is useful in applications such as chromatography columns. In such columns, the orientation of the immobilized macromolecule (e.g., protein) affects the properties of that macromolecule. These affected properties include binding or affinity of the macromolecule to ligands, epitopes, binding sites or the like. Thus, altering the orientation of the macromolecule will permit differential reactivity evidenced by binding, affinity or the like.

This invention has been described in terms of specific embodiments set forth in detail. It should be understood, however, that these embodiments are presented for the purposes of illustration and demonstration, and that therefore the invention is not limited to such embodiments. Modification and variation may be resorted to without departing from the spirit and scope of the invention as claimed.

---

What is claimed is:

1. A coated substrate comprising a substrate having at least a first portion having a surface; and a plurality of mutant heme protein molecules having heme prosthetic groups and preferential binding sites, wherein said preferential binding site of each mutant heme protein molecule was provided by replacement of a surface amino acid residue and said preferential binding site is a reacted amino acid residue coupled with a functional group of said surface of said first portion, such that a coating of said mutant heme protein molecules is formed on said surface of said first portion, and the heme prosthetic groups of said coating of said surface of said first portion have the same spatial relationship with respect to to said surface of said first portion.

2. A coated substrate according to claim 1, wherein said substrate further comprises a second portion having a surface.

3. A coated substrate according to claim 1, wherein said mutant heme proteins are mutated forms of heme proteins selected from the group consisting of cytochrome a, cytochrome b, cytochrome c, myoglobin, hemoglobin or cytochrome P-450.

4. A coated substrate according to claim 1, wherein said functional group is provided by a derivatization reagent.

5. A coated substrate according to claim 1, wherein said substrate comprises a portion having a second mutant protein immobilized thereon.

6. A sensor comprising a coated substrate according to claim 1.

7. A chromatography system comprising a coated substrate according to claim 1.

8. A conductive device comprising a coated substrate according to claim 1.

9. A phase grating comprising a coated substrate according to claim 1.

10. A light modulator comprising a coated substrate according to claim 1.

11. A coated substrate according to claim 1, wherein said mutant heme protein molecules have a site for binding ligands, reporter groups or proteins.

12. A coated substrate according to claim 11, wherein said mutant heme protein molecules having said site for binding are immobilized on said surface to form a first monomolecular layer on said portion, and mutant heme protein molecules are bound to said site for binding to form a second monomolecular layer on said coated substrate.

13. A coated substrate according to claim 2, wherein said surface of said second portion comprises a plurality of mutant heme protein molecules having heme prosthetic groups and preferential binding sites, wherein said preferential binding site of each mutant heme protein molecule has a reacted amino acid residue coupled with a functional group of said surface of said second portion, such that a coating of said mutant heme protein molecules is formed on said surface of said second portion, and the heme prosthetic groups of said coating on said surface of said second portion have the same spatial relationship with respect to said surface of said second portion.

14. A coated substrate according to claim 13, wherein said spatial relationship of said first portion is different than said spatial relations of said second portion.

15. A coated substrate according to claim 1, wherein said heme prosthetic groups of said coating have the same spatial relationship with respect to adjacent heme prosthetic groups of said coating.

16. A coated substrate comprising a substrate having at least one portion having a surface, and a plurality of mutant heme protein molecules immobilized on said surface to form a coating, wherein (A) said mutant heme protein molecules have heme prosthetic groups and preferential binding sites, wherein said preferential binding site of each mutant heme protein molecule was provided by replacement of a surface amino acid residue and said preferential binding site is a reacted amino acid residue coupled with a functional group of said surface to immobilize said mutant heme protein molecule, and (B) said heme prosthetic groups of immobilized mutant heme protein molecules have select spatial relationships with respect to said surface and with respect to adjacent heme prosthetic groups.

17. A process for making a substrate having a coating of mutant heme protein molecules, comprising the steps of:

mutating a heme protein at a select position by replacement of a surface amino acid residue to obtain a preferential binding site on said mutant heme protein; and immobilizing a plurality of said mutant heme proteins on said substrate by reaction of said preferential binding site with a functional group on said substrate so that heme prosthetic groups of said mutant heme proteins have the same spatial relationship with respect to said surface.

* * * * *